(12) United States Patent
Guter et al.

(10) Patent No.: US 12,076,026 B2
(45) Date of Patent: Sep. 3, 2024

(54) METHOD FOR PRODUCING A CUTTING TOOL, AND CUTTING TOOL

(71) Applicant: Kennametal Inc., Latrobe, PA (US)

(72) Inventors: Tim Guter, Fuerth (DE); Jürgen Schwägerl, Vohenstrauss (DE)

(73) Assignee: KENNAMETAL INC., Latrobe, PA (US)

( * ) Notice: Subject to any disclaimer, the term of this patent is extended or adjusted under 35 U.S.C. 154(b) by 922 days.

(21) Appl. No.: 17/113,535

(22) Filed: Dec. 7, 2020

(65) Prior Publication Data

US 2021/0085339 A1  Mar. 25, 2021

Related U.S. Application Data

(62) Division of application No. 16/381,853, filed on Apr. 11, 2019, now Pat. No. 10,952,746.

(51) Int. Cl.
| | | |
|---|---|---|
| *B23B 51/02* | (2006.01) | |
| *A61B 17/16* | (2006.01) | |
| *B23B 51/00* | (2006.01) | |
| *B23P 15/32* | (2006.01) | |

(52) U.S. Cl.
CPC .......... *A61B 17/1615* (2013.01); *B23B 51/00* (2013.01); *B23P 15/32* (2013.01); *B23B 51/02* (2013.01); *B23B 2251/18* (2013.01)

(58) Field of Classification Search
CPC ..... B23B 51/02; B23B 51/00; B23B 2251/18; B23P 15/32; A61B 17/1615; B24B 3/32
USPC ........................................................ 76/108.1
See application file for complete search history.

(56) References Cited

U.S. PATENT DOCUMENTS

| | | | |
|---|---|---|---|
| 2,936,658 A | 5/1960 | Riley | |
| 4,028,987 A | 6/1977 | Wilson | |
| 4,826,368 A | 5/1989 | Tikal et al. | |
| 6,132,149 A | 10/2000 | Howarth et al. | |
| 10,150,168 B2 | 12/2018 | Fukushima et al. | |
| 10,335,866 B2* | 7/2019 | Tempelmeier | .......... B23B 51/02 |
| 11,117,200 B2* | 9/2021 | Bonfiglio | ................ B23B 51/02 |
| 2009/0087275 A1 | 4/2009 | Goulbourne | |
| 2009/0324347 A1* | 12/2009 | Kirby | ...................... B24B 3/065 |
| | | | 407/53 |
| 2010/0028098 A1 | 2/2010 | Shaffer | |

(Continued)

FOREIGN PATENT DOCUMENTS

| | | |
|---|---|---|
| BR | 8905689 | 5/1991 |
| CN | 103379976 A | 10/2013 |

(Continued)

OTHER PUBLICATIONS

Notice of Allowance CN App. No. 110370104A.

(Continued)

*Primary Examiner* — Nhat Chieu Q Do
(74) *Attorney, Agent, or Firm* — Christopher J. Owens

(57) ABSTRACT

A method for producing a cutting tool, in particular a drill bit, is specified wherein the cutting tool has a front end (F) at the front and a rear end (R) toward the rear, wherein a tool tip is formed on the front end (F), a point thinning is ground at the tool tip with a grinding tool, the point thinning being ground to be narrower toward the front than toward the rear. The point thinning is ground with a constant point thinning angle (AW). Furthermore, a corresponding cutting tool is specified.

8 Claims, 7 Drawing Sheets

(56) References Cited

U.S. PATENT DOCUMENTS

| | | | |
|---|---|---|---|
| 2010/0316456 A1 | 12/2010 | George | |
| 2011/0085868 A1 | 4/2011 | Harouche | |
| 2014/0294529 A1 | 10/2014 | Takai | |
| 2017/0203374 A1* | 7/2017 | Tempelmeier | .......... B23B 51/02 |

FOREIGN PATENT DOCUMENTS

| | | | | |
|---|---|---|---|---|
| DE | 102008023856 | | 11/2009 | |
| DE | 102008049509 A1 | | 3/2010 | |
| DE | 102016202104 A1 | | 8/2017 | |
| EP | 1396303 A2 | * | 3/2004 | ............. B23B 51/02 |
| JP | 60-56809 A | | 4/1985 | |
| JP | H06210508 A | | 8/1994 | |
| JP | 2001079707 | | 3/2001 | |
| JP | 2005205526 | | 8/2005 | |
| JP | 2014166660 A | | 9/2014 | |
| WO | WO16047803 | | 3/2016 | |

OTHER PUBLICATIONS

"Special Light Milling Head Produced by 3D Metal Printing", Regional Technological Institute, Faculty of Mechanical Engineering, University of West Bohemia, Univerzitni 8, 306, 14 Plzen, Czech Republic.
Mar. 3, 2022 Office Action (non-US) CN App. No. 110370104A.
Nov. 16, 2020 Notice of Allowance US App. No. 20190314039.
Jun. 11, 2020 Office action (3 months) (US Only) US App. No. 20190314039.
Feb. 25, 2019 Office Action (non-US) DE App. No. 102018205681.

* cited by examiner

METHOD FOR PRODUCING A CUTTING TOOL, AND CUTTING TOOL

CLAIM TO PRIORITY

The application is a divisional application of application Ser. No. 16/381,853, filed Apr. 11, 2019, the entire contents of which are incorporated herein by reference.

RELATED APPLICATION DATA

The present application claims priority pursuant to 35 U.S.C. § 119(a) to German Patent Application No. 102018205681.1 filed Apr. 13, 2018, which is incorporated herein by reference in its entirety.

FIELD

The invention relates to a cutting tool, in particular a drill bit, and to a method for producing such a cutting tool.

BACKGROUND

A drill bit has a number of cutting edges on its front end which during operation bite into the workpiece and remove material. Typically, at least two major cutting edges are formed which are connected in the center of the drill bit by what is known as a chisel edge. During operation, the major cutting edges in each case generate chips which are carried away via flutes which adjoin the major cutting edges. The flutes extend to a certain depth into the drill bit and thereby define a core or core region. The core has a core diameter, which accordingly results from the difference between an overall diameter of the drill bit and the depth of the flutes. The chisel edge is typically formed only in the region of the core.

In contrast to the major cutting edges, the chisel edge does not deploy a cutting effect, but rather displaces the material outwardly from the center. This results in a corresponding expenditure of energy and strong forces which act on the cutting tool, and in a corresponding wear. However, the negative effects of the chisel edge may be reduced by what is known as a point thinning of the cutting edge. The chisel edge is thereby shortened and then typically has a width which is less than the core diameter. The point thinning accordingly leads to a thinning of the core at the front end. To form a point thinning, the drill bit is typically machined at the front end with a grinding wheel. Various advantages then result depending on the specific type and geometry of the point thinning.

SUMMARY

With this as background, it is an object of the invention to specify an improved cutting tool and a corresponding method for its production. In this method, an improved point thinning is to be formed on the cutting tool, which then should lead to a better chip behavior with the cutting tool during operation.

The object is achieved according to the invention by a cutting tool having the features according to claim 1, and by a method having the features according to claim 7. Advantageous embodiments, refinements and variants are the subject-matter of the dependent claims. The embodiments in connection with the method thereby also apply analogously to the cutting tool, and vice versa.

The method serves for the production of a cutting tool. The cutting tool is in particular a drill bit. The cutting tool has a front end on which a tool tip is formed. The cutting tool has a rear end on which in particular a shaft is formed. The cutting tool generally has a body and extends along a longitudinal axis in a longitudinal direction so that the shaft is arranged at the rear end, i.e. behind, and the tool tip is arranged on the front end, i.e. in front. The longitudinal axis is at the same time in particular a central axis of the cutting tool. The shaft serves in particular to hold the cutting tool in a machine tool. Alternatively, the cutting tool is of modular design, with a carrier on the rear end and an insert on the front end, wherein the insert is inserted into the carrier. The tool tip serves for machining material. The cutting tool is in particular a rotary tool and, in operation, rotates in a circumferential direction about the longitudinal axis. The tool tip has at least one major cutting edge which extends from an outer edge of the cutting tool into the interior, and there transitions into a chisel edge. The chisel edge is arranged in the center of the cutting tool, i.e. in particular centrally. In the center, the cutting tool additionally has in particular a core across which the chisel edge extends. In what follows and without any limiting of generality, a cutting tool is assumed which has two major cutting edges which are connected in the center via the chisel edge. The described concepts are not limited to cutting tools having only two major cutting edges. Accordingly, in one variant the cutting tool has more than two major cutting edges.

In the method, a point thinning is ground at the tool tip with a grinding tool. The chisel edge is thereby in particular tapered, meaning that its width is reduced. The grinding tool is in particular a grinding wheel which rotates about an axis of rotation and is brought up to the tool tip in such a way that material is removed there. In particular, material of the core is thereby removed. The grinding tool is directed along a grinding path and in a grinding direction toward the tool tip and is advanced into this. The grinding direction is thus also a direction of movement in which the grinding tool is moved. The axis of rotation is conventionally orthogonal to the grinding direction.

The point thinning is ground in at a constant point-thinning angle. A constant point-thinning angle is achieved in manufacturing by the grinding tool being moved along a straight grinding path, i.e. along a non-curved grinding path. In particular, the grinding path accordingly forms a straight line, at least in the region of the point thinning. The point-thinning angle is that angle which is enclosed by the point thinning together with the longitudinal axis of the cutting tool. In particular, the straight grinding path and the longitudinal axis together also enclose the point-thinning angle. In general, the point thinning has a base which generally extends from the rear to the front and is thereby placed at the point-thinning angle with respect to the longitudinal axis. Viewed at different positions along the longitudinal axis, a cross-sectional profile of the point thinning results in each case in a imaginary plane orthogonal to the longitudinal axis. A cross-sectional profile has in each case a low point at which the distance between the point thinning and the longitudinal axis in the corresponding plane is minimal. In particular, the low points of the point thinning then together form the base. The constant point-thinning angle thus results in particular in a straight profile of the base.

The point thinning is ground narrower toward the front, i.e. toward the front end, than toward the rear, i.e. toward the rear end. The point thinning is accordingly formed to widen toward the rear so that the cutting tool has a point thinning at the front end which expands toward the rear. The grinding tool in particular has a fixed tool width so that, given movement along a grinding path, a corresponding constant grinding width typically results which leads to a constant width of the point thinning. The width of the point thinning is generally measured in a plane orthogonal to the grinding path at a given position along the grinding path. In the present case, the width is now changed, namely, increased toward the rear. The width is thereby also measured at a constant distance from the base of the point thinning, in other words so to speak always at the same height along the base, that is, in each case at the same distance starting from a particular low point. In other words: as measured at a constant distance from the base, the point thinning is ground narrower toward the front than toward the rear.

An essential advantage of the invention is in particular that, due to the special geometry of the point thinning, the chip formation and also the removal of chips during operation of the cutting tool are significantly improved.

On the one hand, an enlarged space for chip formation is provided toward the rear by the widened point thinning; on the other hand, excessive tapering of the chisel edge towards the front is avoided, so that this is correspondingly robust. The point thinning enlarged toward the rear thus advantageously enables an optimal compromise between an optimally robust chisel edge and as optimal a chip formation as possible.

Furthermore, the invention is in particular based on the realization that less space for chip formation is required in the center of the cutting tool than further outward, since less material is removed in the interior due to the lower angular velocity. The point thinning thus does not necessarily need to be ground with a constant grinding width and then have a constant width; rather, it has been recognized in the present instance that a width that increases outwardly is sufficient, and that a smaller width at the center can be selected, so that the tool tip is more robust at the center.

A further advantage is in particular that smaller grinding tools, i.e. grinding tools with smaller grinding width than before, may now also be used. Since only a small width for the point thinning is necessary toward the front, and the width toward the front is advantageously decoupled from the width toward the rear due to the widening, a forward width is expediently chosen which is smaller than is typical, and then the point thinning widens to the typical width toward the rear. The typical width of the point thinning is dependent on the diameter of the cutting tool, and is preferably between 5% and 20% of the diameter. The point thinning toward the rear is preferably wider by a factor of between 1.1 and 2.5 than toward the front, meaning that the point thinning has an expansion of between 1.1 and 2.5.

The grinding tool furthermore has a grinding surface which is in particular outwardly rounded or curved. The grinding surface is thereby rounded or curved with a certain radius, so that the point thinning also correspondingly has a curvature radius which corresponds to the radius of the grinding surface. The point thinning is thus ground into the tool tip as a concave groove or channel.

The grinding width of the grinding tool is generally invariable. In the case of one grinding wheel, the grinding width corresponds in particular to a thickness of the grinding wheel. In a preferred embodiment, toward the rear end, i.e. toward the rear, the point thinning is ground with a width which is greater than the grinding width, in that the tool tip is machined in at least two different positions of the grinding tool. The grinding tool is thus not moved only in an invariant position along a simple grinding path, since in this way only a point thinning with constant width along the grinding path may be formed. Rather, in the present instance the grinding tool is brought against the tool tip in at least two different positions so that the width of the point thinning can be particularly flexibly adjusted. The width of the point thinning is thereby not limited in principle to having the same width as the grinding tool; instead, significantly more possibilities for forming the point thinning now emerge.

In a suitable embodiment, the grinding tool is guided to the tool tip and angled there in order to expand the point thinning toward the rear. The grinding tool is thereby inclined at a certain angle. An expanded point thinning is thereby formed in a simple manner and advantageously by means of the same grinding tool. In particular, this makes use of the fact that, upon tilting the grinding tool, this is moved like a milling tool through the material of the cutting tool, and additional material is thereby removed at the side of the grinding tool, such that the point thinning is wider than the grinding tool as a result. The inclination thereby leads to a corresponding expansion of the point thinning. In particular, a turning on the spot, so to speak, is executed. The grinding tool is therefore initially advanced straight into the tool tip and is moved up to an end position. At the end position, at which the grinding tool is still positioned in the tool tip, the grinding tool is then tilted in order to effect an expansion of the point thinning toward the rear. This is in contrast to a simple translatory movement by means of which only a uniform widening would be achieved.

Alternatively or additionally, in a further suitable embodiment the grinding tool is guided to the tool tip and angled there in order to expand the point thinning toward the rear. The grinding tool is thus advanced into the tool tip along a straight grinding path and tilted while doing so. Starting from the rear, the grinding tool is then thus initially placed at an angle with respect to the grinding path, meaning that the axis of rotation of the grinding tool is specifically not orthogonal to the grinding path. The grinding tool is thus widened as viewed in the direction of the grinding path. The grinding tool thereby has an effective width which is greater than the actual width of the grinding tool. With the forward movement the angle is then decreased so that the effective width is reduced and in particular approaches the actual width. The grinding tool is preferably tilted until it is aligned along the grinding path, meaning until the axis of rotation is orthogonal to the grinding path and the angle is 0°. In this position, the grinding tool has a minimum effective width which corresponds exactly to the actual width. The grinding tool is preferably inclined continuously along the grinding path. In a suitable variant, the grinding path is traversed in the reverse direction, in other words from the front toward the rear, wherein the grinding tool is then correspondingly rotated along the grinding path, i.e. is inclined to a greater extent, meaning that the angle is increased along the grinding path.

For the grinding operation, the grinding tool is generally suitably rotated about a rotation axis, and the grinding surface points in the radial direction, i.e. outwardly orthogonal to the rotation axis. The grinding tool is generally moved in a grinding direction, and the rotation axis is orthogonal to the grinding direction. In the case of the above-described inclination of the grinding tool in order to expand the point thinning, the grinding tool is now tilted or even rotated about a tilt axis. In principle, various inclination axes are suitable here; however, the inclination axis particularly preferably travels orthogonally to the grinding direction and to the rotation axis. With the inclination, the axis of rotation is in other words tilted, whereby a new grinding direction also results which is correspondingly inclined relative to the previous grinding direction. After tilting, the grinding tool is thus placed obliquely with respect to the previous grinding direction. Two different positions of the grinding tool thereby result. The two grinding directions before and after the inclination of the grinding tool are then superimposed, whereby an expanded and in particular wedge-shaped point thinning is produced. The grinding tool is thereby inclined by a certain angle which is also an angle between the two grinding directions. In principle, an embodiment in which the inclination axis corresponds to the grinding direction is also suitable.

In an advantageous embodiment, the grinding tool is guided along a first path segment and in a first grinding direction towards the tool tip; then inclined at the tool tip, in particular as described above; and subsequently guided away from the tool tip along a second path segment and in a second grinding direction. The grinding path accordingly generally consists of two path segments, namely the first path segment along which the grinding tool is guided toward the tool tip, and the second path segment which follows the first path segment and is guided away from the tool tip. The first path segment thus has an end point which corresponds to a starting point of the second path segment, and which at the same time corresponds to an inclination point at which the grinding tool is tilted. Due to this inclination, the two path segments are arranged at an angle relative to one another. However, the two path segments are here in each case inherently straight. As viewed in the longitudinal direction, the inclination point is in particular level with the tool tip, especially level with the chisel edge. In principle, the smallest width of the point thinning arises at the inclination point. The width of the point thinning then increases with increasing distance from the inclination point.

A constant point thinning angle results due to the generally straight movement of the grinding tool, i.e. in that the grinding tool is moved along a straight grinding path or along two straight path segments. Particularly in a variant with a plurality of path segments, these are situated in such a way that a constant point thinning angle results. For this purpose, the grinding tool is in particular inclined such that the path segments and the axis of rotation at the corresponding path segment all lie on a common plane.

The point thinning is preferably formed by means of the same grinding tool in a single grinding pass. This embodiment is particularly simple and requires only a single grinding tool. A tool change is not necessary. Alternatively, however, a configuration is also suitable in which the grinding path is divided up into multiple and in particular two grinding passes, expediently at the inclination point. An embodiment is likewise suitable in principle in which different grinding tools are used.

In a preferred embodiment, the grinding tool is guided along a grinding path with a forward segment on which the grinding tool is guided toward the tool tip, i.e. from back to front, and with a reverse segment along which the grinding tool is guided in the reverse direction and away from the tool tip, i.e. from front to rear. In other words: the grinding tool is first advanced up to an inclination point, then tilted, and finally brought back again. Overall, an in particular V-shaped grinding path results in which the inclination point forms the point of the V. The forward segment corresponds in particular to the first path segment already mentioned above; the reverse path corresponds to the second path segment mentioned in this context. The two path segments are thus arranged at an angle to each other. The path segments are in each case in particular linear, i.e. straight and not curved.

In a suitable embodiment, the point thinning is expanded in that the grinding tool is inclined at the tool tip or during the insertion into this by an angle of more than 0° and at most 10°, preferably at most 5°. The angle is thus merely small. Other regions of the cutting tool are thereby advantageously prevented from being accidentally ground as well during grinding of the point thinning, and in particular also during movement of the grinding tool. An angle of greater than 0° is necessary in order to achieve any expansion at all, i.e. a widening of the point thinning. Due to only the small angle of at most 10°, preferably at most 5°, the space necessary for tilting the grinding tool is advantageously particularly small, so that in particular conventional grinding wheels can continue to be used to produce the point thinning.

The grinding tool is preferably guided along and within a flute to the tool tip, then is tilted to expand the point thinning, and subsequently is guided back again along the same flute. This is based in particular on the consideration that the tool tip is accessible from the flute at an optimal angle for the grinding tool. The grinding tool is then first guided through the flute to the tool tip, i.e. from back to front. The grinding tool thereby follows the grinding path which accordingly leads through the flute, and which in particular is placed or angled at the point-thinning angle relative to the longitudinal axis of the cutting tool, so that the grinding tool penetrates forward into the tool tip upon movement. In principle, a movement in the reverse direction is also suitable.

In a preferred embodiment, the major cutting edge is subdivided into an outer cutting edge segment and an inner cutting edge segment, wherein the inner cutting edge segment forms a part of a border of the point thinning, and the outer cutting edge segment with a chisel edge of the cutting-tool inner cutting edge segment results as part of the border of the point thinning, and connects the outer cutting edge segment with the chisel edge. The border of the point thinning is also referred to as geometry. The major cutting edge in particular transitions into the chisel edge at a cutting edge corner. In a suitable embodiment, the cutting edge corner is ground off so that the width of the chisel edge is reduced. However, the major cutting edge is thereby also modified. In the case of the grinding of the point thinning, the major cutting edge is subdivided into an outer cutting edge segment and an inner cutting edge segment. The outer cutting edge segment is that part of the major cutting edge which remains unaffected by the grinding tool. The inner cutting edge segment results as part of the border of the point thinning and connects the outer cutting edge segment with the chisel edge. In particular, a new cutting edge corner is thereby formed at which the inner cutting edge segment transitions into the chisel edge and which is situated further in toward the center with respect to the original cutting edge corner. Due to the point thinning, in particular a major cutting edge corner is additionally formed at which the outer cutting edge segment transitions into the inner cutting edge segment. In a suitable development, the major cutting edge corner is and will be rounded off, for example will be ground round. Alternatively or additionally, the cutting edge corner also is and will be ground round.

The grinding path is preferably designed such that the above-described grinding of the major cutting edge takes place on the forward path. At the inclination point, the grinding tool is then rotated away from the ground major cutting edge so that an in particular wedge-shaped gap is created between the grinding tool and the inner cutting edge segment. The point thinning is thereby expanded on that side of the grinding tool which is situated opposite the major cutting edge. The grinding tool is subsequently guided rearwardly again and out of the tool tip.

Adjoining the major cutting edge on one side, and generally in the longitudinal direction, is a flute, and on the other side is a flank which points toward the front end. In the direction of rotation, after the major cutting edge the associated flank is bounded by a rearward edge. In the center, the flank is bounded by the chisel edge. Accordingly, a flank is arranged on each side of the chisel edge. At the cutting edge corner, the chisel edge then meets a major cutting edge and a rearward edge. Given a cutting tool without point thinning, two flanks and a flute face accordingly meet one another at the cutting edge corner. After the point thinning has been ground, the cutting edge corner will be displaced further toward the center. At the cutting edge corner, the two flanks and the point thinning now meet one another.

Towards the rear end, the point thinning now opens into the flute, meaning that the flute face adjoins the point thinning, wherein a transition contour is formed which follows a characteristic profile depending on the specific embodiment of the flute and due to the specific embodiment of the point thinning. In a suitable embodiment, the transition contour is undulating and overall follows a W-shaped profile. The W-shaped profile has two troughs which result from the inclination of the grinding tool at the tool tip, i.e. from the different grinding directions on the forward segment and on the rearward segment of the grinding path.

Due to its position at the front of the tool tip, the point thinning adjoins various other functional regions of the cutting tool. In a suitable embodiment, the tool tip has a first major cutting edge which is followed by a flute and a second major cutting edge followed by a flank. The cutting tool thus has at least two major cutting edges. The first and second major cutting edges are connected via a chisel edge. In general, this one flute preferably follows each major cutting edge in the circumferential direction before the respective major cutting edge so that a chip which is removed by means of the major cutting edge is transported away via the associated flute. In the circumferential direction, a major cutting edge is in each case followed by a flank. Further in the circumferential direction, in particular one of the flutes follows a corresponding flank. The first major cutting edge, the chisel edge, the flank after the second major cutting edge, and the flute in front of the first major cutting edge now form a border of the point thinning, meaning that the point thinning is bounded by the aforementioned regions. In particular, only the above-mentioned regions form the complete border of the point thinning.

In general, the point thinning is ground as described above in a grinding direction which, in particular in an embodiment with a plurality of path segments, points forward from the rear. In a preferred embodiment, in cross-section the point thinning has a U-like profile, meaning in particular a U-shaped profile, also referred to as a cross-sectional contour, in cross-section orthogonal to the grinding direction. The profile has two side walls, namely the side legs of the "U", which are in each case connected via a curvature radius with a base, i.e. a transverse leg of the "U". The two curvature radii in particular result from the radius of the grinding surface of the grinding tool and correspond to that radius. In particular, the two curvature radii are identical in size. The width of the point thinning is in particular measured between the side walls. Since the curvature radii along the point thinning in principle remain the same from the front to the rear, an expansion of the point thinning from the front toward the rear is achieved in that the base is wider at the rear than at the front, in other words in that the transverse leg of the "U" becomes longer. On the front end, i.e. toward the front, the two curvature radii preferably merge to form a common curvature radius, so that here these in particular form the base, meaning that the two curvature radii directly transition into one another. Toward the rear, the two curvature radii are then spaced increasingly further apart by an ever-widening base. In a suitable embodiment, the base in cross-section is in a straight line transversal to the grinding direction, in contrast to which the curvature radii are curved.

In an advantageous variant, the point thinning takes the form of a semi-circular recess and has a base with a curvature radius which increases from front to rear. In other words: the point thinning is expanded in that it is not the base that is widened, but rather that the curvature radii are increased toward the rear. The two curvature radii hereby preferably directly transition into one another along the entire point thinning, such that the entire base is thus curved and becomes increasingly wider toward the rear. This is preferably achieved in that the radius of the grinding tool is increased toward the rear, thus along a grinding path from front to back. This is preferably achieved in that, as has already been described above, the grinding tool is placed with respect to the grinding direction, in other words the rotational axis is specifically not orthogonal to the grinding direction and to the grinding path. The grinding tool thereby has an effective width which is greater than the actual width. Accordingly, an effective radius results which is greater than the actual radius. The grinding tool thus, so to speak, casts a shadow, as viewed in the grinding direction, which is larger than the grinding tool. The radius is then reduced from back to rear in that the rotation axis of the grinding tool is rotated toward an orthogonal position with respect to the grinding direction. The shadow of the grinding tool is thereby also reduced accordingly.

The curvature radii are typically dependent on the diameter of the cutting tool, since with different diameters a point thinning with a correspondingly different size is ground by means of grinding tools of different thicknesses having different radii of the grinding surface. The radius, and thus the curvature radii, are preferably within a range between 5% and 10% of the diameter. The widest width of the point thinning, i.e., the rearward width, is preferably 0.5 times to 2 times the radius.

BRIEF DESCRIPTION OF THE DRAWINGS

Exemplary embodiments of the invention are explained in greater detail below with reference to a figure. Shown schematically in each case are.

DETAILED DESCRIPTION

Figure 9:
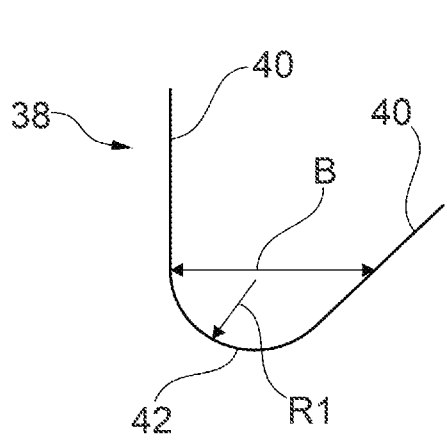
FIG. 9 the point thinning in a first cross-sectional view.
Figure 10:
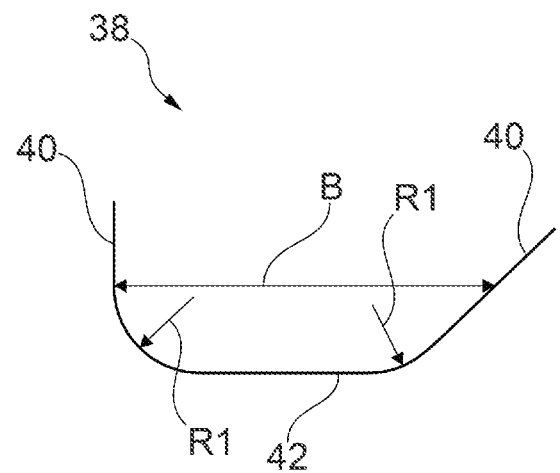
FIG. 10 the point thinning in a second cross-sectional view.
Figure 11:
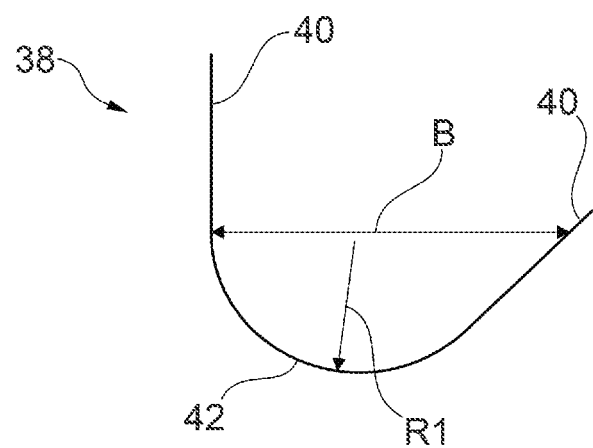
FIG. 11 the point thinning of a variant of the cutting tool in a cross-sectional view.

FIGS. 1 through 10 show various views of a cutting tool 2 with a point thinning 4. Shown in FIG. 11 is a point thinning 4 of a variant of the cutting tool 2. A method for the production of the cutting tool 2 is also described in the following with the aid of the figures.

The cutting tool 2 in the present instance is a rotary tool, especially a drill bit, and has a front end F which points forward and on which is formed a tool tip 6 for machining material. The cutting tool 2 additionally has a rear end R which points rearward and on which is formed a shaft (not shown in detail). The cutting tool 2 generally has a body 8 and extends along a longitudinal axis A in a longitudinal direction so that the shaft is arranged on the rear end R, i.e. toward the rear, and the tool tip 6 is arranged on the front end F, i.e. toward the front. During operation, the cutting tool 2 rotates in a circumferential direction U about the longitudinal axis A.

The tool tip 6 shown has two major cutting edges 10 which in each case extend into the interior from an outer edge 12 of the cutting tool 2 and there transition into a chisel edge 14, and are connected to one another by this. The chisel edge 14 is arranged in the center of the cutting tool 2, i.e. in particular centrally. In the center, the cutting tool 2 has a core 16 across which the chisel edge 14 extends. In a variant (not shown), the cutting tool 2 has more than two major cutting edges 10.

Figure 1:
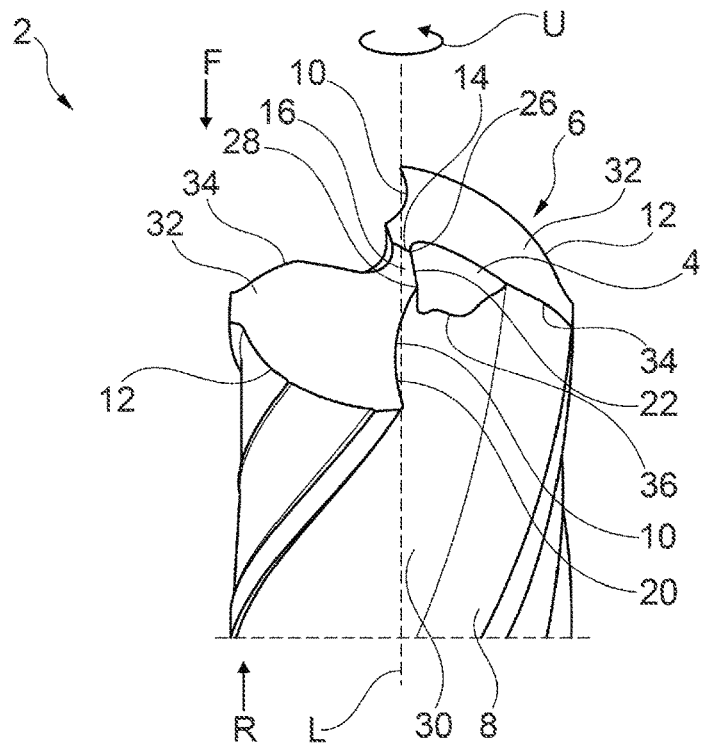
FIG. 1 a cutting tool with a point thinning in a perspective view.
Figure 2:
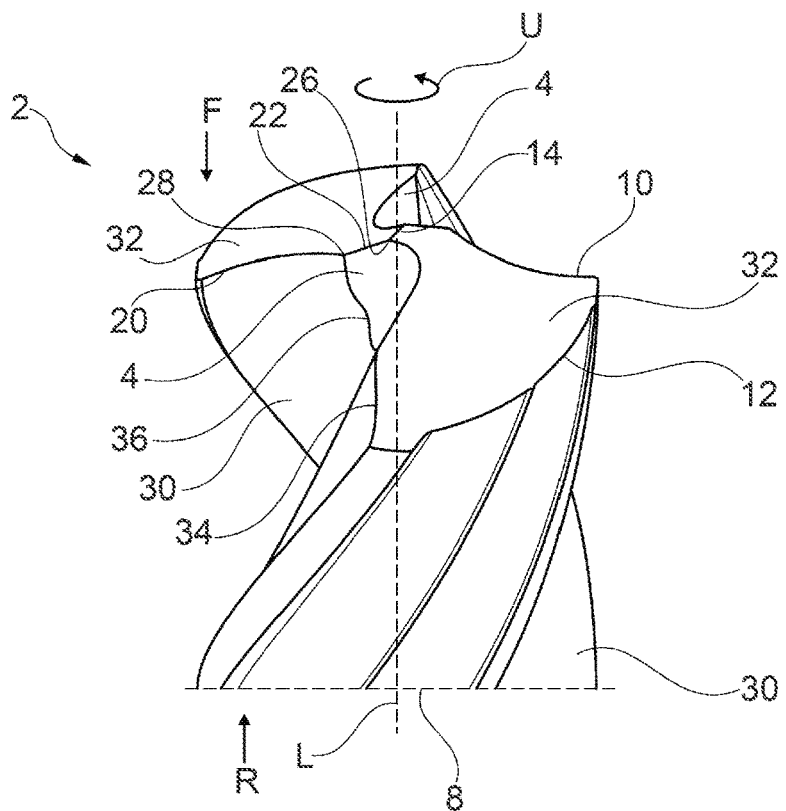
FIG. 2 the cutting tool in a different perspective view.
Figure 3A:
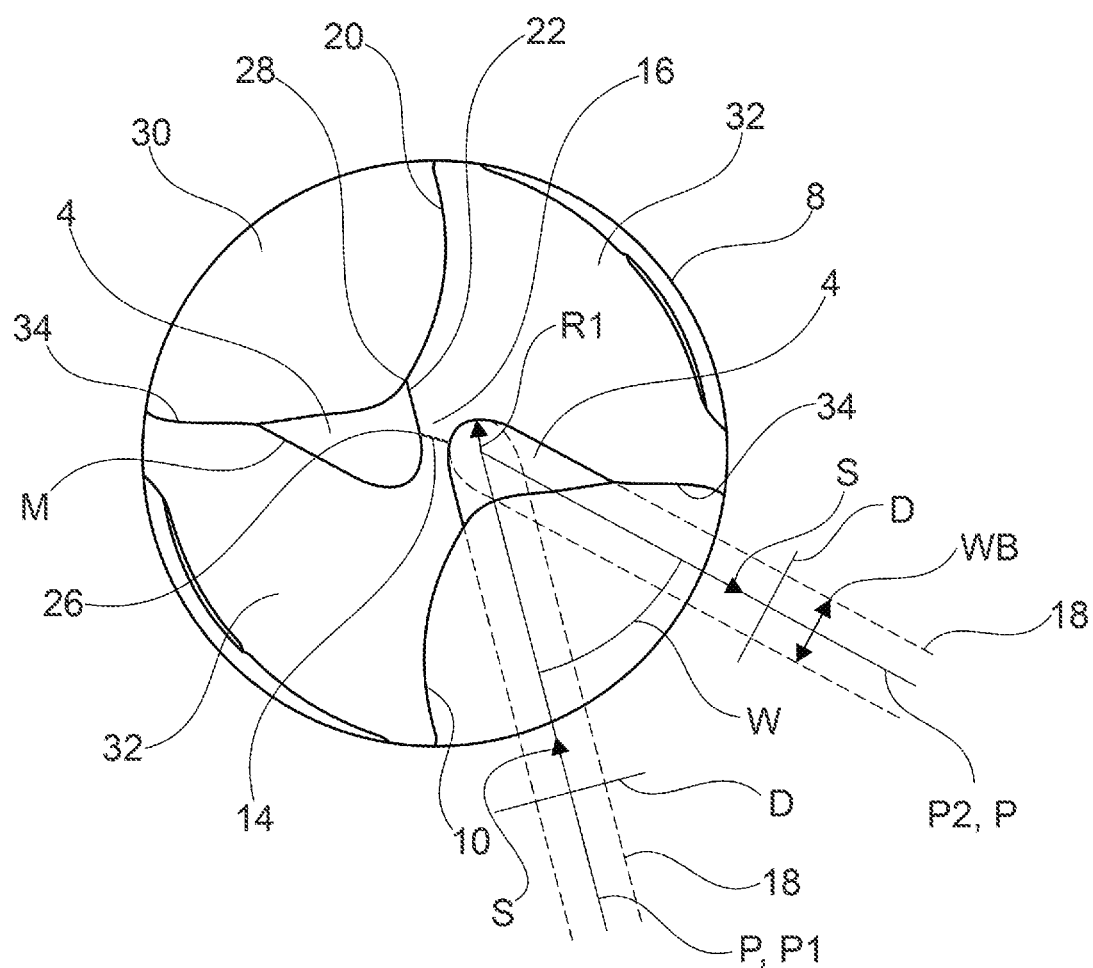
FIG. 3A the cutting tool from the front.

In the cutting tool 2 shown, two point thinnings 4 are formed which are arranged on opposite sides of the chisel edge 4. This is particularly clearly apparent in the two perspective views of FIGS. 1 and 2, which are rotated by 90° relative to one another with respect to the longitudinal axis A, as well as in the front view from the front [sic] in FIG. 3A. During production of the cutting tool 2, the point thinning 4 is ground at the tool tip 6 with a grinding tool 18. The chisel edge 14 is thereby tapered, meaning that its width is reduced. In the present instance, the grinding tool 18 is a grinding wheel which rotates about an axis of rotation D and is placed at the tool tip 6 in such a way that material is removed there. For this purpose, the grinding tool 18 is directed along a grinding path P and in a grinding direction S, i.e. a movement direction, toward the tool tip 6 and is advanced into this. In FIG. 3A, the grinding path P and the grinding tool 18 are shown in two different positions. The axis of rotation D is orthogonal to the grinding direction S. The grinding tool 18 has a grinding surface which in particular is rounded or curved outwardly with a specific radius R1, such that the point thinning 4 also has a curvature radius R1 which corresponds to the radius R1 of the grinding surface. The point thinning 4 is thus ground into the tool tip 6 as a concave groove or channel.

In the present instance, the point thinning 4 is formed in a single grinding pass by means of the same grinding tool 18. As shown in FIG. 3A, the grinding tool 18 is here guided along the V-shaped grinding path P, namely initially along a forward segment P1 on which the grinding tool 18 is guided toward the tool tip 6, i.e. from back to rear, and then along a reverse segment P2 along which the grinding tool 18 is guided in the reverse direction and away from the tool tip 6, i.e. from front to rear. The forward segment P1 also generally corresponds to a first path segment; the reverse path P2 generally corresponds to a second path segment. Both path segments are arranged angled relative to one another at an angle W and are in each case linear, i.e. straight and not curved.

Figure 3B:
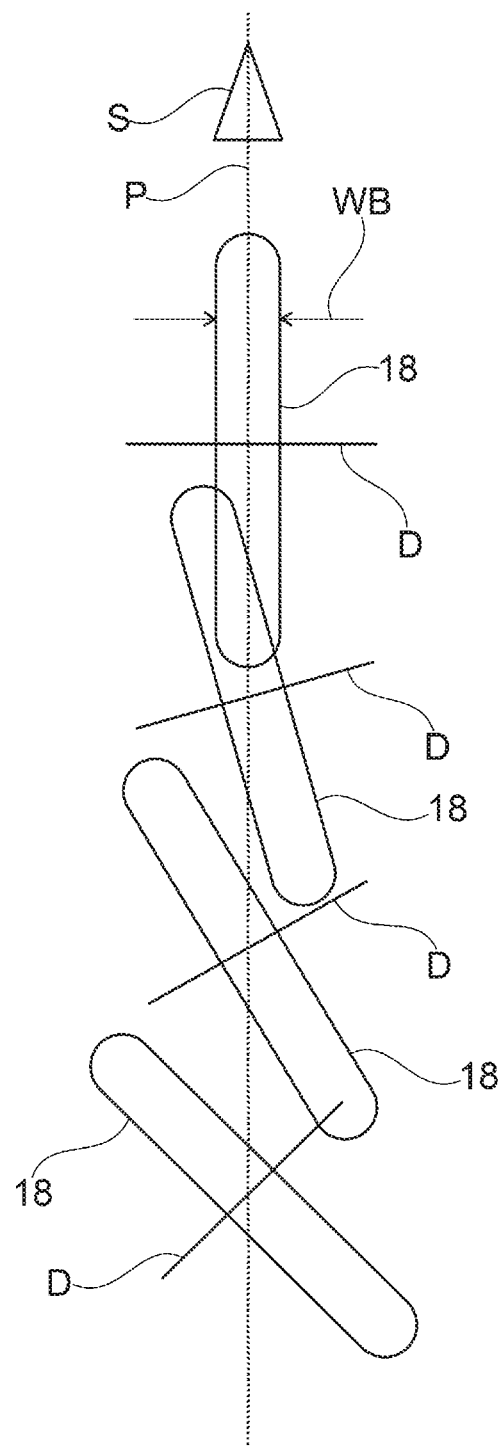
FIG. 3B an alternative way of producing the point thinning.

Shown in FIG. 3B is the principle of an alternative production method which in principle may also be combined with the aforementioned variant. Here the grinding path P is not split into a plurality of straight grinding paths P1, P2, as in FIG. 3A, but is instead only a single straight line. To produce a point thinning 4 that is tapered toward the front, in FIG. 3B the grinding tool 18 is directed toward the tool tip 6 (not shown here) and is here inclined. The grinding tool 18 is thus advanced into the tool tip 6 along an inherently straight grinding path P and is inclined while doing so. This is illustrated in FIG. 3B by multiple depictions of the grinding tool 18 at various longitudinal positions along the grinding path P. Beginning at the rear, the grinding tool 18 is initially placed at an angle W with respect to the grinding path P, meaning that the axis of rotation D of the grinding tool 18 is specifically not orthogonal to the grinding path P. The grinding tool 18 thereby has an effective width which is larger than the actual width WB of the grinding tool 18. During movement in the grinding direction S, i.e. in this case forward, the angle W is then reduced so that the effective width is reduced. The grinding tool 18 is in the present case inclined until it is aligned along the grinding path P, i.e. until the rotation axis D is orthogonal to the grinding path P and the angle W is 0°. Here the grinding tool 18 is also continuously inclined along the grinding path P. The grinding path P shown corresponds to the first path segment P1, for example, or lies between the two path segments P1, P2. Other embodiments are also suitable.

Figure 4:
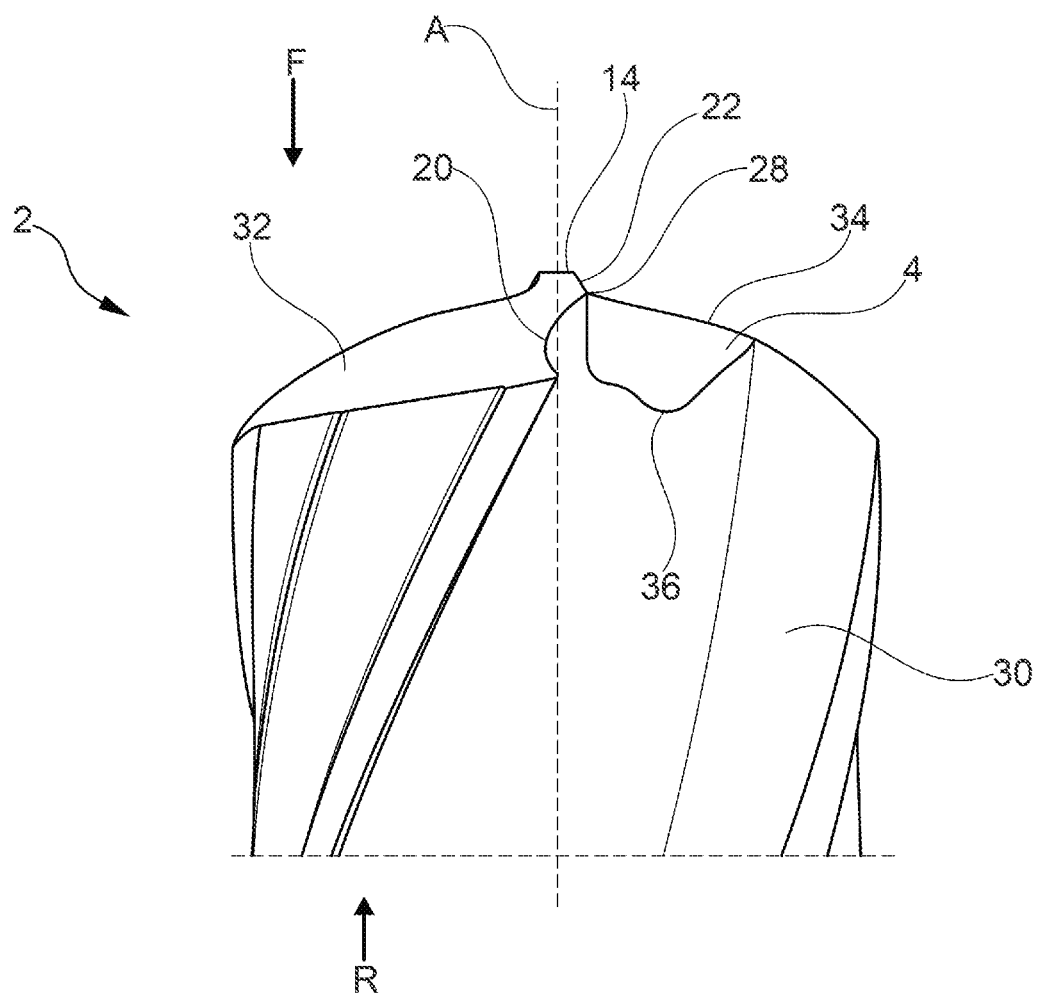
FIG. 4 the cutting tool in a side view.
Figure 5:
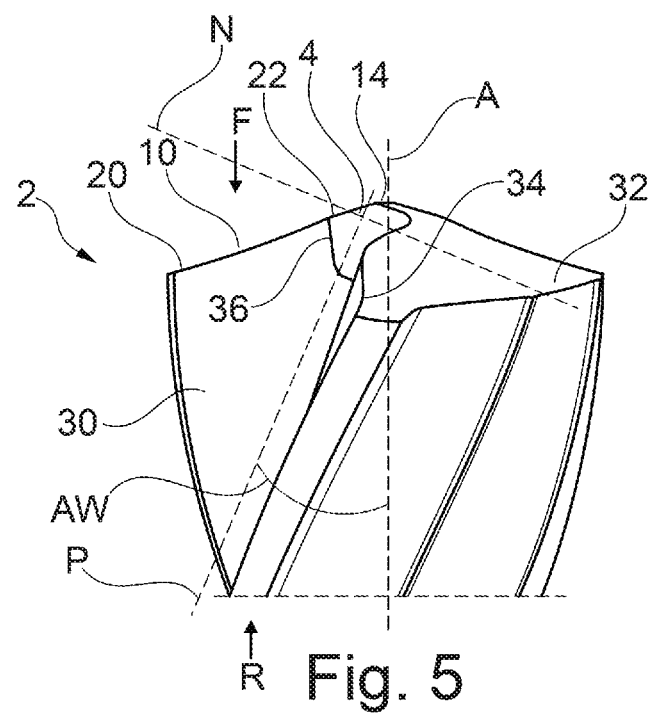
FIG. 5 the cutting tool in a different side view.

Due to its special production, the point thinning 4 has a correspondingly specific geometry which also leads to a characteristic course of a respective major cutting edge 10. This is apparent on the one hand from FIGS. 1, 2, and 3, on the other hand also from the two side views of FIGS. 4 and 5, which show the cutting tool 2 in two views rotated relative to one another by 90° about the longitudinal axis A. FIG. 4 thereby shows a view along one of the major cutting edges 10 on one of the rearward edges 34; conversely, FIG. 5 shows a view of one of the major cutting edges 10. The grinding path S is also shown in FIG. 5. Due to the view selected, the two path segments P1, P2 in FIG. 5 overlap each other. It can be particularly readily seen here that the point thinning 4 is formed with a constant point-thinning angle AW. Given the production procedure according to FIG. 3A, this results in particular in the axis of rotation D and the grinding direction S on the two path segments P1, P2 thus all falling together in one plane.

During the grinding of the point thinning 4, the major cutting edge 10 is divided into an outer cutting edge segment 20 and an inner cutting edge segment 22. The outer cutting edge segment 20 is that part of the major cutting edge 10 which remains unaffected by the grinding tool 18. This is also clearly apparent from FIG. 3A. The inner cutting edge segment 22 results as part of the border M of the point thinning 4 and connects the outer cutting edge segment 20 with the chisel edge 14. A new cutting edge corner 26 is thereby formed at which the inner cutting edge segment 22 transitions into the chisel edge 14, and which lies further toward the center. Due to the point thinning 4, a major cutting edge corner 28 is additionally formed at which the outer cutting edge segment 20 transitions into the inner cutting edge segment 22. In a development (not shown), the major cutting edge corner 28 or the cutting edge corner 26 or both are rounded off.

Adjoining a respective major cutting edge 10 on one side, and generally in the longitudinal direction, is a flute 30, and on the other side is a flank 32 which points toward the front end F. In the circumferential direction U, after the major cutting edge 10 the associated flank 32 is bounded by a rearward edge 34. In the center, the flank 32 is bounded by the chisel edge 14. Accordingly, a flank 32 is in each case arranged on each side of the chisel edge 14. At a cutting edge corner 26, the chisel edge 14 then meets a major cutting edge 10 and a rearward edge 34, and accordingly the two flanks 32 and the point thinning 4 also meet one another.

At the rear end R, the point thinning 4 now opens into the flute 30, wherein a transition contour 36 is formed which follows a characteristic course depending on the specific embodiment of the flute 30 and due to the specific embodiment of the point thinning 4. In the exemplary embodiment shown, the transition contour 36 is undulating and follows overall a W-shaped course which has two troughs which result from the different grinding directions S on the grinding path P. Due to its position at the front of the tool tip 6, the point thinning 4 adjoins various other functional regions of the cutting tool 2. In the present instance, the point thinning 4 is bounded by one of the major cutting edges 10, the chisel edge 14, and one of the flanks 32 in addition to the flute 30. These regions form the border M of the point thinning 4.

The point thinning 4 is ground to be narrower toward the front, i.e. toward the front end F, than toward the rear, i.e. toward the rear end R, and accordingly is formed so as to expand toward the rear. The grinding tool 18 in particular has a fixed tool width so that, during movement along the grinding path P, a correspondingly constant grinding width WB typically results which customarily leads to a constant width B of the point thinning 4. The width B of the point thinning 4 is generally measured in a plane orthogonal to the grinding path S at a given position along the grinding path P. Cross-sections along such planes orthogonal to the grinding path P are shown in each case in FIGS. 9 and 10. FIG. 9 here shows a cross-section along the forward path P1 and which is situated further forward than the cross-section shown in FIG. 10. Clearly apparent is the greater width B of the point thinning 4 at the location of the grinding path S as shown in FIG. 10. The point thinning 4 is now ground with a width B toward the rear, said width B being greater than the grinding width WB in that the tool tip 6 is machined in at least two different positions of the grinding tool 2. The grinding tool 2 is thus not moved only along a simple and in particular a straight grinding path P, because only a point thinning 4 of constant width B may thereby be formed along the grinding path P. Rather, as is apparent in FIG. 3A, the grinding tool 2 in the present instance is brought to the tool tip 6 in two different positions, inclined there by an angle W, and the point thinning 4 thereby expanded towards the rear. The inclination here leads to a corresponding expansion of the point thinning 4.

In the case of the described inclination of the grinding tool 18, this is tilted about an inclination axis N which respectively runs orthogonally to the grinding direction S and to the rotation axis D so that, during tilting, the rotation axis D is tilted, whereby a new grinding direction S also results which is correspondingly inclined with respect to the previous grinding direction S. The inclination axis is shown in FIG. 5. Two different positions of the grinding tool 18 thereby result. The two grinding directions S before and after the inclination of the grinding tool 18 are then superimposed, whereby an expanded and wedge-shaped point thinning 4 is produced. In the exemplary embodiment shown, the inclination of the grinding tool 18 and the expansion of the point thinning 4 are represented greatly exaggerated. In fact, the angle W during inclination is at most 1°. However, an angle W of greater than 0° is necessary here in order to achieve any expansion at all, i.e. a widening of the point thinning 4.

Figure 6:
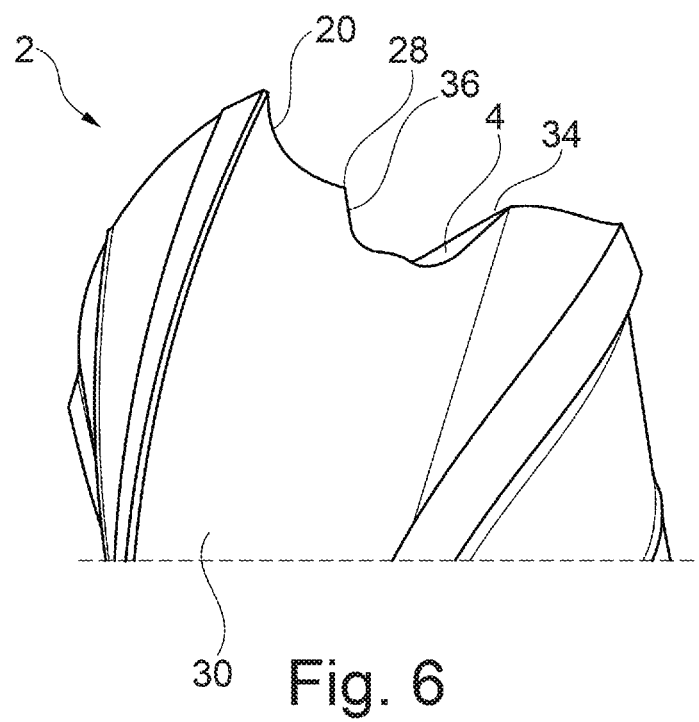
FIG. 6 the cutting tool in a view along a first path segment.
Figure 7:
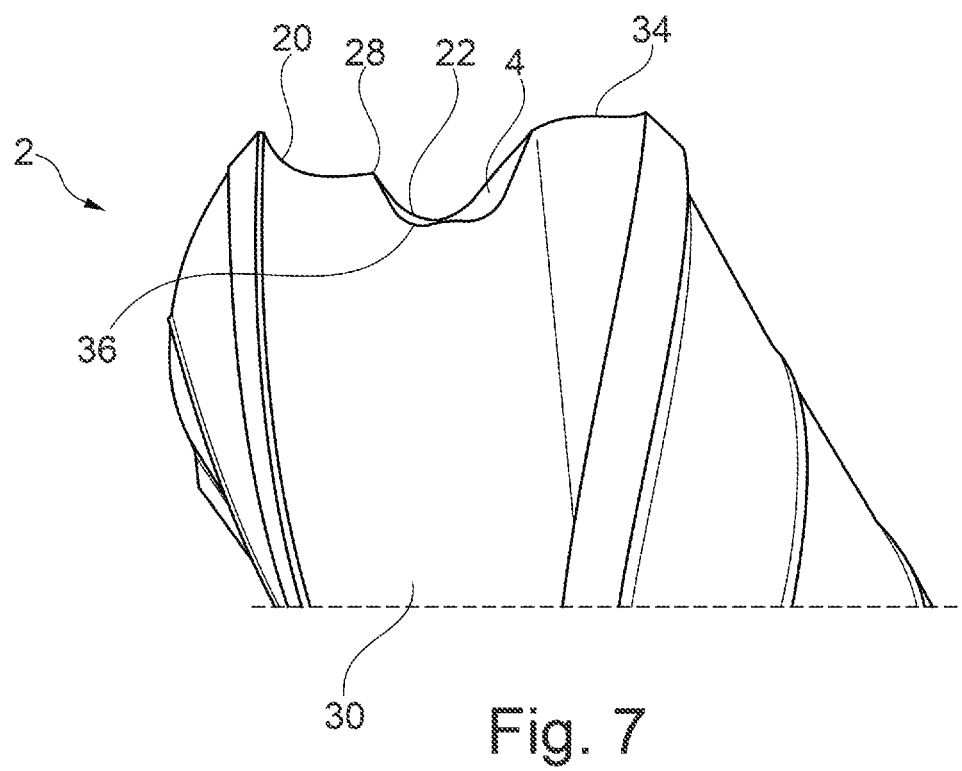
FIG. 7 the cutting tool in an oblique view through a flute.
Figure 8:
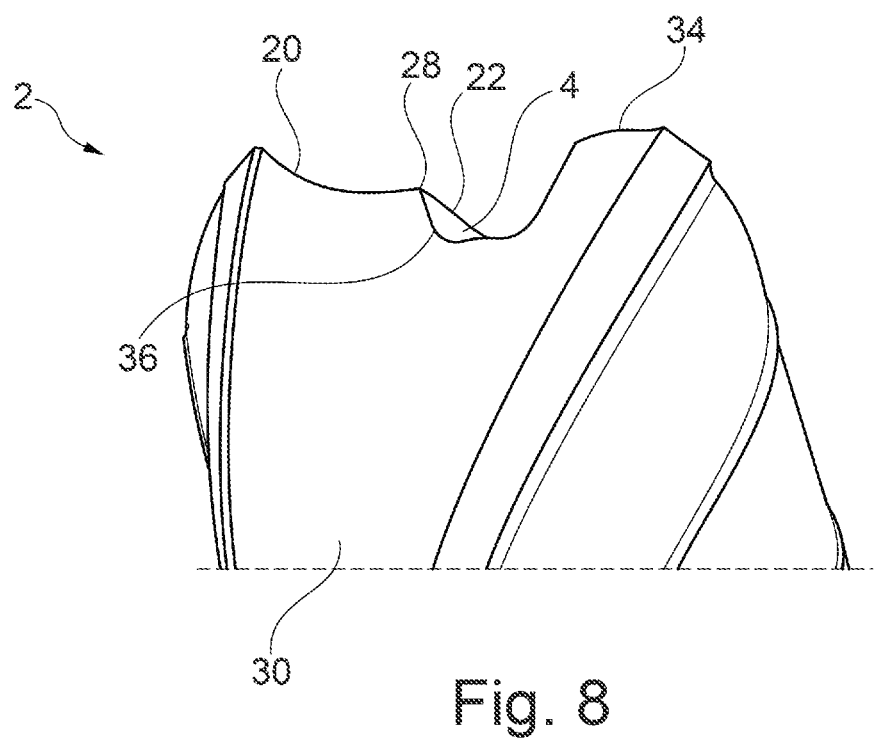
FIG. 8 the cutting tool in a view along a second path segment.

The point thinning 4, and especially the transition contour 36, are also particularly clearly apparent in the oblique views of FIGS. 6, 7, and 8. FIG. 6 here shows a view approximately along the forward segment P1 and in the grinding direction S; FIG. 8 shows a view approximately along the reverse segment P2 and correspondingly opposite the grinding direction S; FIG. 7 shows a view of the point thinning 4 at an angle W between the two path segments P1, P2. As has already been described, the W-shaped transition contour 36 shown only results due to the specific shape of the flute 30, and in the present instance is also correspondingly strongly pronounced due to the angle W that has been greatly increased for the purpose of clarity. However, as viewed in cross-section orthogonally to the grinding direction S, and at correspondingly small angles W, the point thinning 4 generally has a U-like profile 38 as shown in the FIGS. 9, 10, and 11. The profile 38 has two side walls 40, namely the side legs of the "U", which respectively are connected via a curvature radius R1 with a base 42, i.e. a transverse leg of the "U". At the front end F, i.e. at the front, the two curvature radii R1 coincide as shown in FIG. 9, so that here these also form the base 42. Toward the rear, the two curvature radii R1 are then spaced apart from one another by an ever-widening base 42, as shown in FIG. 10.

FIG. 11 shows the profile 38 of a variant of the cutting tool 2, in which variant the point thinning 4 is designed as a semicircular recess and has a base 42 with a curvature radius R1 which increases from front to back. FIG. 9 here also applies to the variant, and is arranged further forward in relation to the cross-section in FIG. 11. In the comparison between FIGS. 9 and 11, it is then clear that the point thinning 4 is widened in such a way that the curvature radius R1 is increased toward the rear. In contrast to FIG. 10, the entire base 42 is thus continuously curved and becomes increasingly wider towards the rear.

The invention claimed is:

1. A method for producing a drill bit having a front end (F) and a rear end (R), the front end (F) having a tool tip, the method comprising grinding a point thinning at the tool tip with a grinding tool that rotates about an axis of rotation (D), wherein, in a single grinding pass, the grinding tool is guided along a grinding path (P) along in a forward segment (P1) in which the grinding tool is guided toward the tool tip with the axis of rotation (D) orthogonal to a first grinding direction (S), and then the grinding tool is guided along the grinding path (P) in a reverse segment (P2) in which the grinding tool is guided away from the tool tip with the axis of rotation (D) orthogonal to a second grinding direction (S), wherein the point thinning is ground with a constant point-thinning angle (AW) with respect to a longitudinal axis (A) of the drill bit, and wherein a base of the point thinning has a width that is narrower at the front end of the drill bit and is wider distal the front end the tool tip of the drill bit.

2. The method according to claim 1, wherein the point thinning has a generally U-shaped profile having the base and two side walls that are connected to the base with a curvature radius (R1).

3. The method according to claim 1, wherein the forward segment (P1) corresponds to a first path segment and the reverse segment (P2) corresponds to a second path segment, and wherein the grinding tool is guided along a V-shaped grinding path (P) in which the first path segment and the second path segment are angled relative to one another at an angle (W).

4. The method according to claim 3, wherein the angle (W) is greater than 0° and less or equal to 10°.

5. The method according to claim 3, wherein the angle (W) is greater than 0° and less or equal to 5°.

6. The method according to claim 1, wherein the grinding tool is guided along the grinding path (P) such that the point thinning forms a transition contour between the point thinning and a flute of the drill bit.

7. The method according to claim 6, wherein the transition countour is undulating and follows a W-shaped path having two troughs that result from the forward segment (P1) in which the grinding tool is guided toward the tool tip with the axis of rotation (D) orthogonal to a first grinding direction (S) and the second segment (P2) in which the grinding tool is guided away from the tool tip with the axis of rotation (D) orthogonal to a first grinding direction (S).

8. The method according to claim 1, wherein the drill bit further comprises a major cutting edge, a chisel edge, a flank and a flute, and wherein the point thinning forms a border (M) between the major cutting edge, the chisel edge, the flank and the flute of the drill bit.

\* \* \* \* \*